US012752129B2

(12) United States Patent
Passerini et al.

(10) Patent No.: US 12,752,129 B2
(45) Date of Patent: Oct. 6, 2026

(54) SYSTEMS AND METHODS FOR PLANNING OF CARDIAC RADIATION THERAPY

(71) Applicant: Varian Medical Systems, Inc., Palo Alto, CA (US)

(72) Inventors: Tiziano Passerini, Plainsboro, NJ (US); Puneet Sharma, Princeton Junction, NJ (US)

(73) Assignee: Varian Medical Systems, Inc., Palo Alto, CA (US)

(*) Notice: Subject to any disclaimer, the term of this patent is extended or adjusted under 35 U.S.C. 154(b) by 1097 days.

(21) Appl. No.: 17/855,171

(22) Filed: Jun. 30, 2022

(65) Prior Publication Data

US 2024/0001147 A1 Jan. 4, 2024

(51) Int. Cl.

| | |
|---|---|
| ***A61N 5/10*** | (2006.01) |
| ***A61B 5/00*** | (2006.01) |
| ***A61B 5/055*** | (2006.01) |
| ***A61B 5/11*** | (2006.01) |
| ***A61B 6/03*** | (2006.01) |

(Continued)

(52) U.S. Cl.

CPC ............ *A61N 5/1037* (2013.01); *A61B 34/10* (2016.02); *A61N 5/1039* (2013.01); *A61B 2034/105* (2016.02)

(58) Field of Classification Search

CPC ................ A61N 5/1037; A61N 5/1039; A61N 5/1049; A61B 34/10; A61B 2034/105; A61B 6/032; A61B 5/055; A61B 5/0022; A61B 5/0044; A61B 5/1128; A61B 5/0036; A61B 5/367; A61B 5/7485; A61B 6/503;

(Continued)

(56) References Cited

U.S. PATENT DOCUMENTS 9,129,053 B2 9/2015 Mansi et al.
9,245,091 B2 1/2016 Voigt et al.
(Continued)

FOREIGN PATENT DOCUMENTS

JP 2016-515843 A 6/2016
WO WO-2021/163227 8/2021

OTHER PUBLICATIONS

International Search Report and Written Opinion on PCT App. PCT/US2023/025153 dated Sep. 19, 2023 (11 pages).

(Continued)

*Primary Examiner* — Carrie R Dorna
*Assistant Examiner* — Joshua Daryl D Lannu
(74) *Attorney, Agent, or Firm* — Foley & Lardner LLP

(57) ABSTRACT

Systems and methods for predicting a location of a target heart region for cardiac ablation can include one or more processors generating a 3D model of a heart of a patient based on medical images of the patient, and estimating, using the 3D model of the heart and electrophysiology data of the patient, one or more mechanical properties that drive motion of the patient's heart. The one or more processors can generate, using the 3D model and the one or more mechanical properties, a simulated motion pattern of the patient's heart over at least a portion of a cardiac cycle, and identify a region of interest (ROI) of the heart of the patient to be radiated. The one or more processors can determine, using the simulated motion pattern of the heart of the patient, a location of the ROI at a predefined time instance within the cardiac cycle.

23 Claims, 6 Drawing Sheets

(51) Int. Cl.

| | |
|---|---|
| ***A61B 6/50*** | (2024.01) |
| ***A61B 34/10*** | (2016.01) |
| ***G16H 30/20*** | (2018.01) |
| ***G16H 30/40*** | (2018.01) |
| ***G16H 40/63*** | (2018.01) |
| ***G16H 40/67*** | (2018.01) |
| ***G16H 50/20*** | (2018.01) |
| ***G16H 50/30*** | (2018.01) |

(58) Field of Classification Search
CPC ........ G16H 40/63; G16H 50/30; G16H 40/67; G16H 30/20; G16H 30/40; G16H 50/20
See application file for complete search history.

(56) References Cited

U.S. PATENT DOCUMENTS

| | | | |
|---|---|---|---|
| 9,463,072 | B2 | 10/2016 | Comaniciu et al. |
| 11,241,590 | B2 | 2/2022 | Sumanaweera et al. |
| 2015/0042646 | A1 | 2/2015 | Comaniciu et al. |
| 2016/0022375 | A1 | 1/2016 | Blake et al. |
| 2016/0220311 | A1 | 8/2016 | Mansi et al. |
| 2020/0179722 | A1* | 6/2020 | Packer ................. A61N 5/1037 |
| 2021/0137384 | A1* | 5/2021 | Robinson ................. A61B 8/14 |

OTHER PUBLICATIONS

Examination report No. 1 dated Aug. 12, 2025 for AU App. 2023297833 (2 pages).
Krebs et al., Learning a Probabilistic Model for Diffeomorphic Registration. Mar. 17, 2019. https://doi.org/10.48550/arXiv.1812.07460.
Zhang et al., Cardiac radiotherapy induces electrical conduction reprogramming 1n the absence of transmural fibrosis (2021)12:5558 I https://doi.org/10.1038/s41467-021-25730-0 I www.nature.com/naturecommunications.
Zheng et al., Four-Chamber Heart Modeling and Automatic Segmentation for 3-D Cardiac CT Volumes Using Marginal Space Learning and Steerable Features. IEEE Transactions on Medical Imaging, vol. 27, No. 11, Nov. 2008.
Office Action issued in corresponding Japanese Patent Application No. 2024-576943 dated Nov. 20, 2025.

* cited by examiner

SYSTEMS AND METHODS FOR PLANNING OF CARDIAC RADIATION THERAPY

TECHNICAL FIELD

The present application relates generally to systems and methods for planning of cardiac radiation therapy. Specifically, the present application relates to systems and methods for estimating patient specific motion patterns of a beating heart over a cardiac cycle, where the estimated motion patterns are used to estimate the location of a region of interest of the heart over the cardiac cycle.

BACKGROUND

Cardiac ablation is usually an invasive medical procedure used to treat a variety of heart conditions, such as atrial fibrillation (AFib), atrial flutter, atrial tachycardia, ventricular tachycardia (VT), atrioventricular nodal reentrant tachycardia (AVNRT), paroxysmal supraventricular tachycardia (PSVT), Wolff-Parkinson-White syndrome, or heart tumors. The standard radio cardiac procedure involves a doctor inserting a catheter into a patient's body to access the patient's heart. Heat or extreme cold is then applied to destroy abnormal areas of the heart and disrupt the abnormal electrical signals traveling through the heart. The procedure may be risky at least for some types of patients, and typically requires monitoring patients in the intensive care unit afterward. Some of the risks associated with standard radio ablation include bleeding or infection at the site where the catheter was inserted, blood vessel damage, heart valve damage, new or worsening arrhythmia, slow heart rate, blood clots, stroke or heart attack, pulmonary vein stenosis, damage to the kidneys from contrast used during the procedure, and/or death in rare cases.

Cardiac radiotherapy ablation (also referred to as cardiac radioablation) is a noninvasive form of cardiac ablation. Instead of a catheter, a radiation dose is used to target the abnormal areas of the heart to destroy them. The use of radiation relives some of the risks associated with the invasive procedure and provides relief for high-risk heart patients who most likely have run out of other options. However, cardiac radioablation has its own risks and comes with its own challenges. Among them is the risk of destroying surrounding healthy tissue, particularly in the heart region. Such risk calls for accurate radiation in terms of radiation area(s) and radiation dose(s).

Prior to the radiotherapy ablation procedure, radiotherapy treatment planning is performed. The objective of treatment planning is to optimize radiation angles and/or radiation doses for various angles to ensure that a high radiation dose is delivered to the target region and a low radiation dose is applied to intervening tissues.

SUMMARY

Embodiments described herein relate to improved prediction of locations of target heart regions for cardiac ablation. A simulated motion pattern that accurately mimics or reproduces the motion of a patient's heart can be generated. The simulated motion pattern allows for determining the location of a target heart region at various time instances of a cardiac cycle. The simulated motion pattern or simulated states of the heart can be used by a cardiac radiotherapy planning system to accurately plan the radiation of the target heart region while minimizing radiation to surrounding or intervening healthy tissue.

According to one aspect, a method of predicting a location of target heart region for cardiac ablation can include one or more processors generating a three-dimensional (3D) model of a heart of a patient based on medical images of the patient, and estimating, using the 3D model of the heart and electrophysiology data of the patient, one or more mechanical properties that drive motion of the heart of the patient. The method can include the one or more processors generating, using the 3D model and the one or more mechanical properties, a simulated motion pattern of the heart of the patient over at least a portion of a cardiac cycle, and identifying a region of interest (ROI) of the heart of the patient to be radiated. The method can include determining, using the simulated motion pattern of the heart of the patient, a location of the ROI at a predefined time instance within the cardiac cycle.

In some implementations, the one or more mechanical properties include contraction forces and relaxation forces of the heart of the patient. In some implementations, the medical images can include a sequence of image frames acquired over a time interval, and the method can further include the one or more processors determining, using the sequence of image frames, an estimated motion pattern of the heart of the patient over the cardiac cycle. Determining the estimated motion pattern can include tracking displacements of a discrete set of points of the heart over the sequence of image frames or estimating, using a machine learning model, a displacement field using the sequence of image frames.

The method can include determining, using the estimated motion pattern of the heart of the patient, one or more estimated positions of one or more points of the heart of the patient at a time point of the cardiac cycle, and determining, using the simulated motion pattern of the heart of the patient, one or more simulation positions of the one or more points of the heart of the patient at the time point of the cardiac cycle. The method can include computing one or more point-wise distances between the one or more simulation positions and the one or more estimated positions, updating the one or more mechanical properties of the heart of the patient, upon determining that the one or more point-wise distances exceed a threshold value, and updating the simulated motion pattern of the heart of the patient based on the updated one or more mechanical properties. The method can include repeating the steps of determining the one or more simulation positions, computing the one or more point-wise distances, updating the one or more mechanical properties and updating the simulated motion pattern of the heart of the patient until the one or more point-wise distances are below the threshold value.

Determining the one or more estimated positions can include the one or more processors deforming, according to the estimated motion pattern of the heart of the patient, a 3D model of the heart corresponding to a time instance t0 to determine an estimated 3D model of the heart corresponding to a time instance t1, and identifying the one or more estimated positions on the estimated 3D model of the heart corresponding to the time instance t1. The estimated 3D model is indicative of an estimated state of the heart at the time instance t1. Determining the one or more simulation positions can include the one or more processors deforming, according to the simulated motion pattern of the heart of the patient, the 3D model of the heart corresponding to the time instance t0 to determine a simulated 3D model of the heart corresponding to the time instance t1, and identifying the one or more simulation positions on the simulated 3D model of the heart corresponding to the time instance t1. The simulated 3D model is indicative of a simulated state of the heart at the time instance t1. The method can include repeating the steps of determining the one or more estimated positions and determining the one or more simulation positions for a plurality of time instance pairs (t0, t1) corresponding to pairs of consecutive image frames in the sequence of image frames, computing a plurality of point-wise distances between simulation positions and corresponding estimated positions across the plurality of time instance pairs (t0, t1), and updating the one or more mechanical properties of the heart of the patient, upon determining that the plurality of point-wise distances exceed the threshold value.

In some implementations, updating the one or more mechanical properties of the heart of the patient can include generating a plurality of second simulated motion patterns of the heart corresponding to various variations of the one or more mechanical properties and various variations of electrical properties of the heart, determining, for each second simulated motion pattern, one or more corresponding simulation positions of the one or more points of the heart of the patient at the time point of the cardiac cycle, computing, for each second simulated motion pattern, one or more corresponding point-wise distances between the one or more corresponding simulation positions and the one or more estimated positions, selecting a second simulated motion pattern of the plurality of second simulated motion patterns based on the one or more corresponding point-wise distances, and updating the one or more mechanical properties according to variations of the one or more mechanical properties corresponding to the selected second simulated motion pattern. In some implementations, the ROI includes one or more segments of a standardized N-segment model where N is an integer. In some implementations, the method can further include modeling immobilization conditions to be applied to the patient during a cardiac ablation procedure as boundary conditions incorporated in the simulated motion pattern of the heart of the patient.

According to another aspect, a system for predicting a location of target heart region for cardiac ablation can include one or more processors and a memory to store computer code instructions. The computer code instructions, when executed, can cause the one or more processors to generate a three-dimensional (3D) model of a heart of a patient based on medical images of the patient, estimate, using the 3D model of the heart and electrophysiology data of the patient, one or more mechanical properties that drive motion of the heart of the patient, generate, using the 3D model and the one or more mechanical properties, a simulated motion pattern of the heart of the patient over a cardiac cycle, identify a region of interest (ROI) of the heart of the patient to be radiated, and determine, using the simulated motion pattern of the heart of the patient, a location of the ROI at a predefined time instance within the cardiac cycle.

In some implementations, the one or more mechanical properties include contraction forces and relaxation forces of the heart of the patient. In some implementations, the medical images can include a sequence of image frames acquired over a time interval, and the one or more processors can further determine, using the sequence of image frames, an estimated motion pattern of the heart of the patient over the cardiac cycle. In determining the estimated motion pattern, the one or more processors can track displacements of a discrete set of points of the heart over the sequence of image frames or estimate, using a machine learning model, a displacement field using the sequence of image frames.

The one or more processors can determine, using the estimated motion pattern of the heart of the patient, one or more estimated positions of one or more points of the heart of the patient at a time point of the cardiac cycle, and determine, using the simulated motion pattern of the heart of the patient, one or more simulation positions of the one or more points of the heart of the patient at the time point of the cardiac cycle. The one or more processors can compute one or more point-wise distances between the one or more simulation positions and the one or more estimated positions, update the one or more mechanical properties of the heart of the patient, upon determining that the one or more point-wise distances exceed a threshold value, and update the simulated motion pattern of the heart of the patient based on the updated one or more mechanical properties. The one or more processors can repeat the steps of determining the one or more simulation positions, computing the one or more point-wise distances, updating the one or more mechanical properties and updating the simulated motion pattern of the heart of the patient until the one or more point-wise distances are below the threshold value.

When determining the one or more estimated positions, the one or more processors can deform, according to the estimated motion pattern of the heart of the patient, a 3D model of the heart corresponding to a time instance t0 to determine an estimated 3D model of the heart corresponding to a time instance t1, and identify the one or more estimated positions on the estimated 3D model of the heart corresponding to the time instance t1. The estimated 3D model is indicative of an estimated state of the heart at the time instance t1. When determining the one or more simulation positions, the one or more processors can deform, according t0 the simulated motion pattern of the heart of the patient, the 3D model of the heart corresponding to the time instance t0 to determine a simulated 3D model of the heart corresponding to the time instance t1, and identify the one or more simulation positions on the simulated 3D model of the heart corresponding to the time instance t1. The simulated 3D model is indicative of a simulated state of the heart at the time instance t1. The one or more processors can repeat the steps of determining the one or more estimated positions and determining the one or more simulation positions for a plurality of time instance pairs (t0, t1) corresponding to pairs of consecutive image frames in the sequence of image frames, computing a plurality of point-wise distances between simulation positions and corresponding estimated positions across the plurality of time instance pairs (t0, t1), and updating the one or more mechanical properties of the heart of the patient, upon determining that the plurality of point-wise distances exceed the threshold value.

In some implementations, when updating the one or more mechanical properties of the heart of the patient the one or more processors can generate a plurality of second simulated motion patterns of the heart corresponding to various variations of the one or more mechanical properties and various variations of electrical properties of the heart, determine, for each second simulated motion pattern, one or more corresponding simulation positions of the one or more points of the heart of the patient at the time point of the cardiac cycle, compute, for each second simulated motion pattern, one or more corresponding point-wise distances between the one or more corresponding simulation positions and the one or more estimated positions, select a second simulated motion pattern of the plurality of second simulated motion patterns based on the one or more corresponding point-wise distances, and update the one or more mechanical properties according to variations of the one or more mechanical properties corresponding to the selected second simulated motion pattern. In some implementations, the ROI includes one or more segments of a standardized N-segment model where N is an integer. In some implementations, the one or more processors can further model immobilization conditions to be applied to the patient during a cardiac ablation procedure as boundary conditions incorporated in the simulated motion pattern of the heart of the patient.

According to yet another aspect, a computer readable medium can include computer code instructions stored thereon. The computer code instructions when executed can cause one or more processors to generate a three-dimensional (3D) model of a heart of a patient based on medical images of the patient, estimate, using the 3D model of the heart and electrophysiology data of the patient, one or more mechanical properties that drive motion of the heart of the patient, generate, using the 3D model and the one or more mechanical properties, a simulated motion pattern of the heart of the patient over a cardiac cycle, identify a region of interest (ROI) of the heart of the patient to be radiated, and determine, using the simulated motion pattern of the heart of the patient, a location of the ROI at a predefined time instance within the cardiac cycle.

Figure 1:
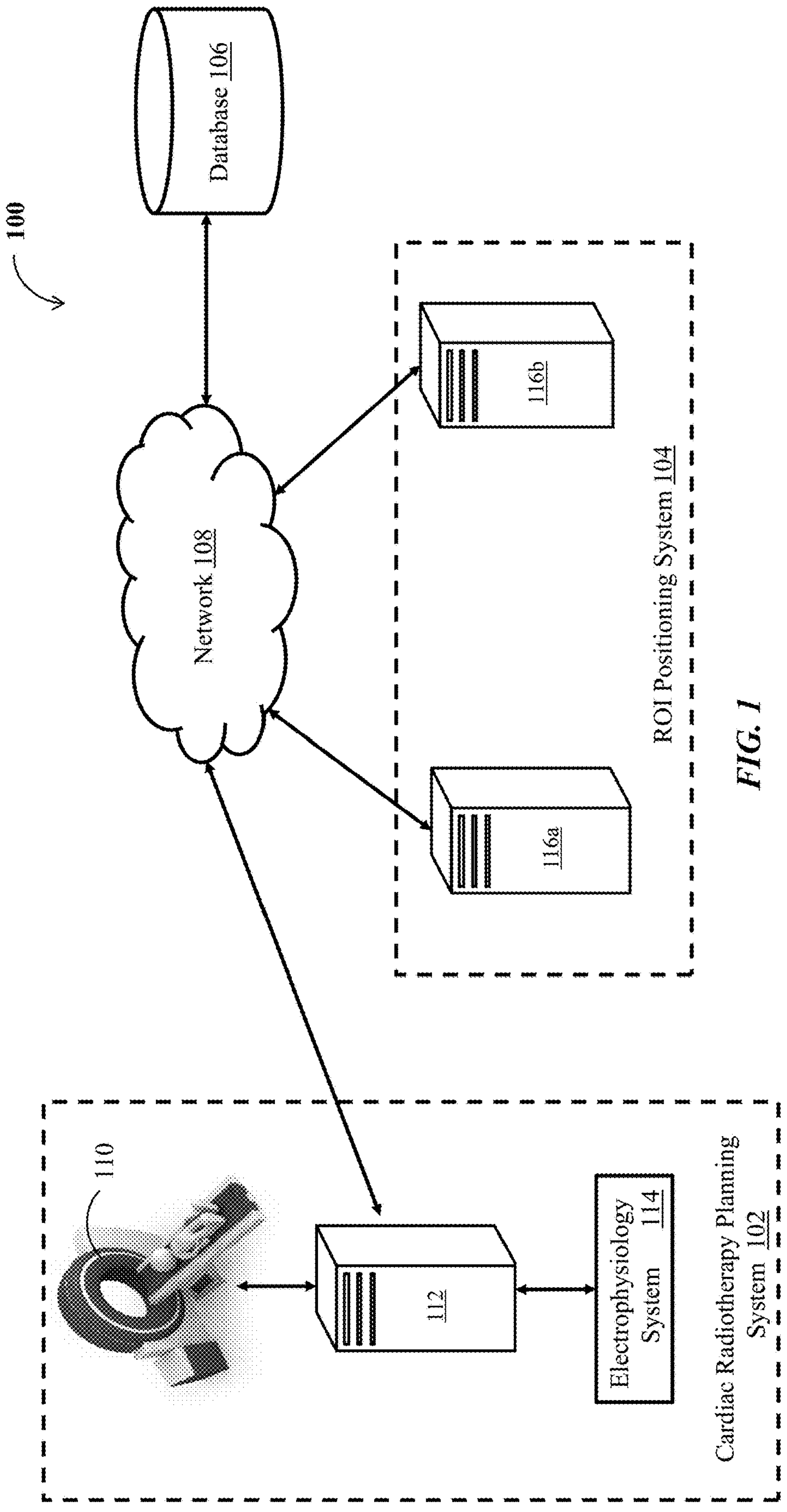
FIG. 1 shows a block diagram illustrating a computer environment for implementing methods and processes described herein, according to an embodiment.

Some or all of the figures are schematic representations for purposes of illustration. The foregoing information and the following detailed description include illustrative examples of various aspects and implementations, and provide an overview or framework for understanding the nature and character of the claimed aspects and implementations. The drawings provide illustration and a further understanding of the various aspects and implementations, and are incorporated in and constitute a part of this specification.

DETAILED DESCRIPTION

Following below are more detailed descriptions of various concepts related to, and implementations of, methods, apparatuses, and systems for predicting locations of heart regions for planning cardiac radiotherapy ablation. The various concepts introduced above and discussed in greater detail below may be implemented in any of numerous ways as the described concepts are not limited to any particular manner of implementation. Examples of specific implementations and applications are provided primarily for illustrative purposes.

Cardiac radiotherapy ablation holds the promise of being a safer and more effective ablation strategy compared to catheter-based ablation, mainly due to its non-invasiveness nature and the potential ability of targeting the full thickness of the myocardium. However, to make such a promise a reality various challenges are still to be overcome. These challenges are mainly due to the strict requirements with regard to radiation accuracy. The heart is composed of multiple structures at risk, including coronary arteries and valves. These structures are to be spared from radiation (or to be subjected to a relatively low radiation) to avoid permanent and serious damage to the heart. At the same time, the treatment aims to apply a sufficiently high radiation dose to abnormal regions of the heart in order to destroy or at least change the characteristics (e.g., electrophysiology properties) of these regions. This tradeoff makes the radiation therapy an intricate and complex task in general, and more so for the heart.

During radiotherapy planning, various parameters of the external radiation beam are determined to achieve a desired radiation dose distribution. These parameters include, for example, angles and intensities of the radiation beam. The external beam parameters depend on the size, shape and location of the target region at the time of radiation, the geometry and nature of surrounding or intervening tissue and the prescription dose. However, the heart is a continuously moving organ, and the radiation is to be applied while the heart is moving. Furthermore, the motion of various regions of the heart, including the target region, is much more complex than the motion of other organs, e.g., brain or spine among other organs, for which radiation therapy has been shown to be an effective choice. In addition, radiation therapy has the potential to cause toxicity to healthy cardiac tissue. The target region which represents the abnormal region to be radiated is also referred to herein as region of interest (ROI).

Technical problems associated with cardiac radiotherapy ablation relate to the difficulty to accurately target the region of interest, and the challenge of determining the optimal level of radiation to maximize ablation success and minimizing toxicity. In this disclosure, the targeting of the region of interest is addressed by describing systems, methods and devices for accurately predicting the location of the target region over at least a portion of a cardiac cycle. The determined location of the ROI can be used during radiotherapy planning to guarantee accurate targeting of the ROI. In existing techniques, the heart motion is not accurately estimated. As a result, an overestimated target volume is usually used to account for uncertainties in the location of target volume (or ROI) at any time instance of the cardia cycle.

FIG. 1 illustrates an example computer environment 100 for planning of cardiac radiation therapy, according an example embodiment. In brief overview, the computer environment 100 can include a cardiac radiotherapy planning system 102, a region of interest (ROI) positioning system 104, a database 106 and a communication network 108. The cardiac radiotherapy planning system 102 can include an imaging device 110, an electrophysiology system 114 and one or more computing devices 112. The ROI positioning system 104 can include one or more computing devices such as computing devices 116*a* and 116*b*, referred to herein individually or collectively as computing device(s) 116. Computing device(s) 116 is/are configured to predict locations of ROIs. The cardiac radiotherapy planning system 102, the ROI positioning system 104 and the database 106 can be communicatively coupled to each other through the communication network 108.

The communication network 108 may include a local area network (LAN), a wireless local area network (WLAN), a metropolitan area network (MAN), a wide area network (WAN), the Internet, a cellular network, a network of other type or a combination thereof. The network 108 may include both wired and wireless communications according to one or more standards and/or via one or more transport mediums. The communication over the network 108 may be performed in accordance with various communication protocols such as Transmission Control Protocol and Internet Protocol (TCP/IP), User Datagram Protocol (UDP), and IEEE communication protocols.

The cardiac radiotherapy planning system 102 can include one or more imaging devices 110, an electrophysiology system 112 and one or more computing devices 114. The imaging device 110 can include a computed tomography (CT) scanner, a magnetic resonance (MR) scanner, a positron emission tomography (PET) scanner or a combination thereof, among others. The imaging device 110 can acquire medical images of the heart of a patient over at least a portion of a cardiac cycle. In some implementations, the imaging device 110 can acquire a sequence of images depicting the heart motion or deformation over the cardiac cycle or a portion thereof. The acquired medical images can include CT images, computed tomography angiography (CTA) images, MR images, PET images, other types of medical images, or a combination thereof.

The electrophysiology system 112 is configured to perform electrophysiological studies of the patient, for example, to evaluate the heart's electrical system and to diagnose abnormal heart beats or arrhythmia. The electrophysiology system 112 can include one or more catheters, a plurality of wire electrodes and a computing device connected to the wire electrodes to record electrical signals. A doctor inserts the catheter in a vein in the groin of the patient, and then insert the wire electrodes into the patient's heart via the catheter and the vein. Natural electric pulses of the heart can travel through the wire electrodes to be recorded by the computing device of the electrophysiology system 112. In some implementations, the electrophysiology system 114 can include a plurality of electrocardiogram (ECG) electrodes to be placed on the surface of the patient's body (e.g., chest) via a multi-electrode vest. Natural electric pulses of the heart can travel through the wire electrodes to be recorded by the computing device of the electrophysiology system 114. The computing device of the electrophysiology system 114 can send electrical signals through the electrodes to stimulate the heart tissue to try to cause the abnormal heart rhythm.

The computing device 112 can receive medical images from the imaging device 110 and electrophysiological study data from the electrophysiology system 112. The computing device 112 can also obtain other medical data of the patient, such as electrocardiogram (ECG) data, blood pressure data and/or other patient data. The computer device 112 can be configured to run or execute radiation simulations as part of the radiotherapy planning. A radiotherapy planner can use the computer device 112 to simulate one or more sets of radiotherapy parameters to determine which set of parameters leads to a desired radiation dose distribution. The computer device 112 can also send acquired patient data, such as the medical images and the electrophysiology study data the database 106.

The ROI positioning system 104 (or respective computing device(s) 116) can be configured to use the acquired medical images and electrophysiology study data of the patient to estimate realistic motion patterns of the heart or ROI that would reflect the dynamic positions of the ROI across at least part of the cardiac cycle. In estimating the motion pattern of the heart or ROI, the ROI positioning system 104 estimate and use mechanical properties, such as contracting forces/pressures and relaxing forces/pressures, of the heart that drive the motion of the heart during a cardiac cycle or a portion thereof. The ROI positioning system 104 (or respective computing device(s) 116) can generate a simulated model that mimics motion patterns of the heart and the ROI over at least a portion of the cardiac cycle. The functional properties of the ROI positioning system 104 (or respective computing device(s) 116) are discussed in further detail below in relation with FIGS. 3-6B.

In some implementations, the computing device(s) 116 can be configured to execute computer instructions to perform any of the methods described herein or operations thereof. The computing device(s) 116 may generate and display an electronic platform to display information indicative of, or related to, motion patterns of the heart and/or ROI. The electronic platform may include a graphical user interface (GUI) for receiving input data and/or displaying predicted motion patterns and/or location of the heart or ROI. An example of the electronic platform generated and hosted by the computing device(s) 106 may be a web-based application or a website configured to be displayed on different electronic devices, such as mobile devices, tablets, personal computer, and the like.

While FIG. 1 shows a network based implementation, it is to be noted that methods described herein can be implemented by a single computing device that receives the medical images and electrophysiological data of the patient and predicts motion patterns and/or dynamic locations of the ROI according to methods described herein. The computer environment 100 is not necessarily confined to the components described herein and may include additional or alternative components, not shown for brevity, which are to be considered within the scope of the embodiments described herein. For instance, the computer environment 100 may include additional or alternative databases, for example within the cardiac radiotherapy planning system 102 or within the ROI positioning system 104. Also the number of computing devices within the cardiac radiotherapy planning system 102 or within the ROI positioning system 104 may vary according to various implementations.

Figure 2:
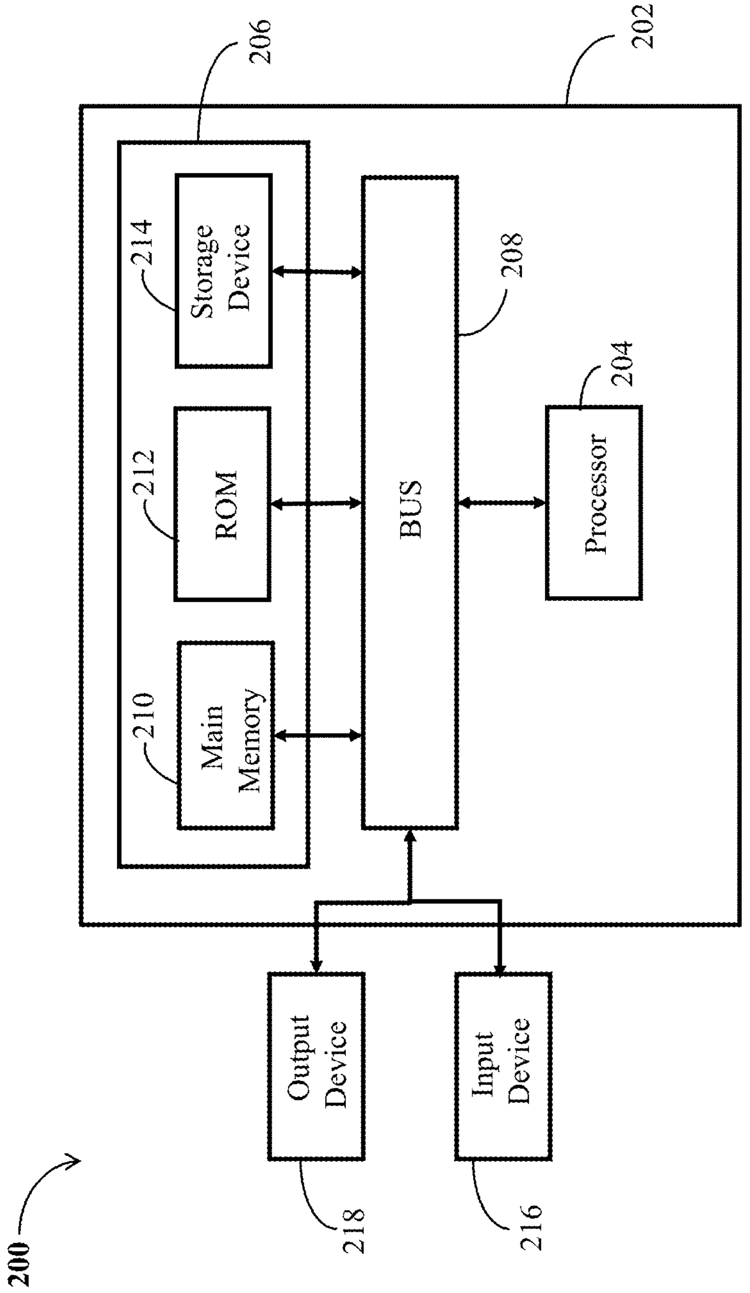
FIG. 2 is a block diagram depicting one implementation of a system architecture, according to an embodiment.

Referring to FIG. 2, a block diagram depicting one implementation of a system architecture for a computing system 200 that may be employed to implement methods described herein is shown, according to example embodiments. The computing system 200 can include a computing device 202. The computing device 202 can represent an example implementation of any of the devices 112 and/or 116 of FIG. 1. The computing device 202 can include, but is not limited to, a computed tomography (CT) scanner, a medical linear accelerator device, a desktop, a laptop, a hardware computer server, a workstation, a personal digital assistant, a mobile computing device, a smart phone, a tablet, or other type of computing device. The computing device 202 can include a one or more processors 204 to execute computer code instructions, a memory 206 and a bus 208 communicatively coupling the processor 204 and the memory 206.

The one or more processors 204 can include a microprocessor, a general purpose processor, a multi-core processor, a digital signal processor (DSP) or a field programmable gate array (FPGA), an application-specific integrated circuit (ASIC) or other type of processor. The one or more processors 204 can be communicatively coupled to the bus 208 for processing information. The memory 206 can include a main memory device 210, such as a random-access memory (RAM) other dynamic storage device, coupled to the bus 208 for storing information and instructions to be executed by the processor 204. The main memory device 210 can be used for storing temporary variables or other intermediate information during execution of instructions (e.g., related to methods described herein such as method 400) by the processor 204. The computing device 202 can include a read-only memory (ROM) 212 or other static storage device coupled to the bus 208 for storing static information and instructions for the processor 204. For instance, the ROM 212 can store medical images of patients, for example, received as input. The ROM 212 can store computer code instructions related to, or representing an implementation of, methods described herein. A storage device 214, such as a solid state device, magnetic disk or optical disk, can be coupled to the bus 208 for storing (or providing as input) information and/or instructions.

The computing device 202 can be communicatively coupled to, or can include, an input device 216 and/or an output device 218. The computing device 202 can be coupled via the bus 218 to the output device 218. The output device 218 can include a display device, such as a Liquid Crystal Display (LCD), Thin-Film-Transistor LCD (TFT), an Organic Light Emitting Diode (OLED) display, LED display, Electronic Paper display, Plasma Display Panel (PDP), or other display, etc., for displaying information to a user. The output device 218 can include a communication interface for communicating information to other external devices. An input device 216, such as a keyboard including alphanumeric and other keys, may be coupled to the bus 208 for communicating information and command selections to the processor 204. In another implementation, the input device 216 may be integrated within a display device, such as in a touch screen display. The input device 216 can include a cursor control, such as a mouse, a trackball, or cursor direction keys, for communicating direction information and command selections to the processor 204 and for controlling cursor movement on the display device.

According to various implementations, the methods described herein or respective operations can be implemented as an arrangement of computer code instructions that are executed by the processor(s) 204 of the computing system 200. The arrangement of computer code instructions can be read into main memory device 210 from another computer-readable medium, such as the ROM 212 or the storage device 214. Execution of the arrangement of computer code instructions stored in main memory device 210 can cause the computing system 200 to perform the methods described herein or operations thereof. In some implementations, one or more processors 204 in a multi-processor arrangement may be employed to execute the computer code instructions representing an implementation of methods or processes described herein. In some other implementations, hard-wired circuitry may be used in place of or in combination with software instructions to effect illustrative implementation of the methods described herein or operations thereof. In general, implementations are not limited to any specific combination of hardware circuitry and software. The functional operations described in this specification can be implemented in other types of digital electronic circuitry, in computer software, firmware, hardware or a combination thereof.

Figure 3:
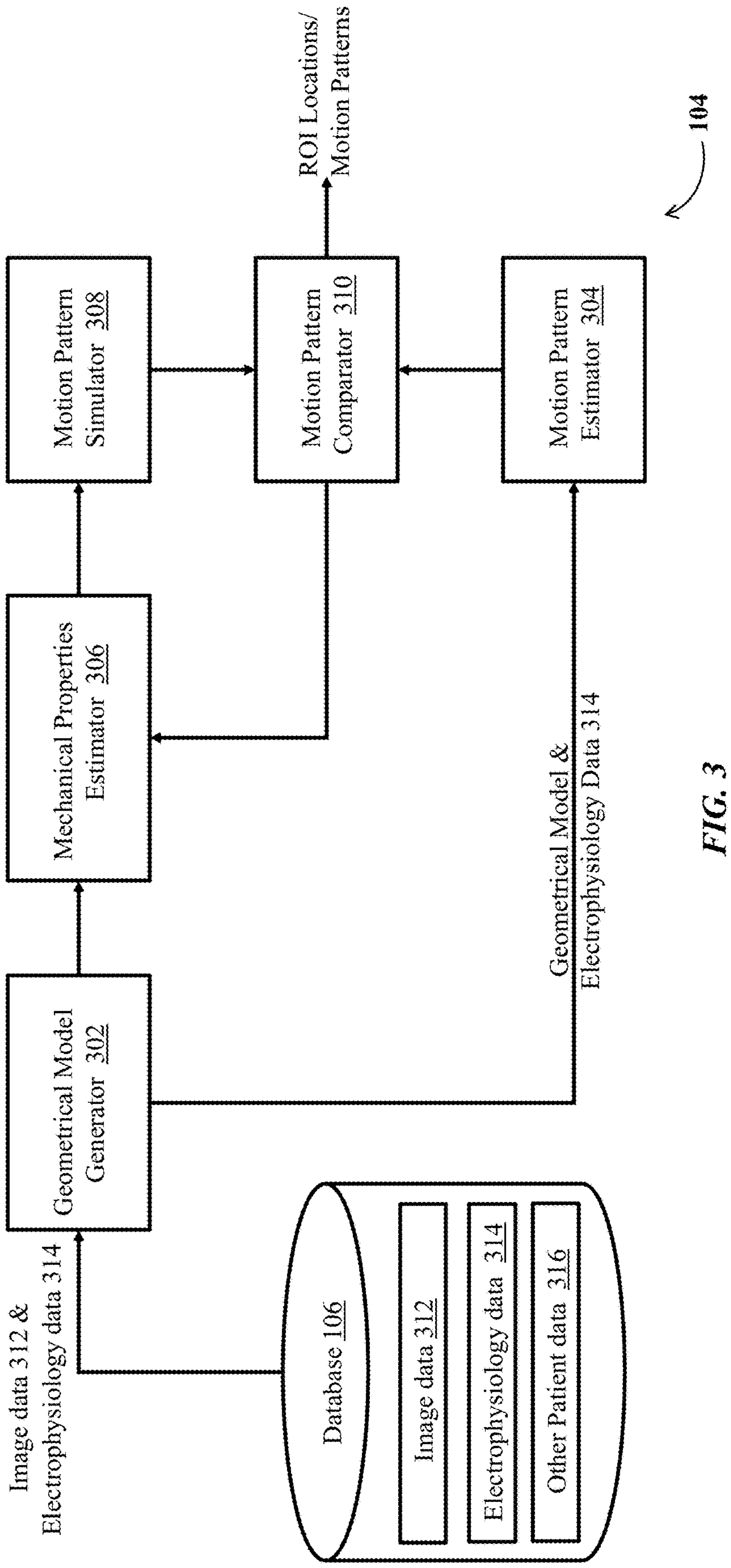
FIG. 3 is a block diagram of a system for predicting locations of target heart regions, according to an embodiment.

Referring now to FIG. 3, a block diagram of ROI positioning system 104 for predicting locations of target heart regions is shown, according to an embodiment. The ROI positioning system 104 is a system for accurately predicting locations of target heart regions, according to an embodiment. In brief overview, the ROI positioning system 104 can include a geometrical model generator 302, a motion pattern estimator 304, a mechanical properties estimator 306, a motion pattern simulator 308 and a motion pattern comparator 310. The ROI positioning system 104 may include or may be connected to database 106. The database 106 can include image data 312, electrophysiology data 314 and/or other patient data 316. The image data 312 can include CT images, CTA images and/or other medical images of the patient. The electrophysiology data 314 can include electrophysiology study data of the patient depicting electrical activities of the patient's heart over at least a cardiac cycle or a portion thereof. The other patient data 316 can include blood pressure data, ECG data, medical history data, demographic data or a combination thereof.

Each of the components 302, 304, 306, 308 and/or 310 can be implemented as a software component, hardware component, firmware component or a combination of software, firmware and/or hardware. For instance, any of these components can be implemented as computer code instructions that are executed by one or more processors, e.g., processor 204, to perform respective functional steps or processes. Any of the components 302, 304, 306, 308 and/or 310 can be implemented as a digital circuitry. The functional steps or processes associated with each of these components are described in further detail below in relation with FIG. 4.

Figure 4:
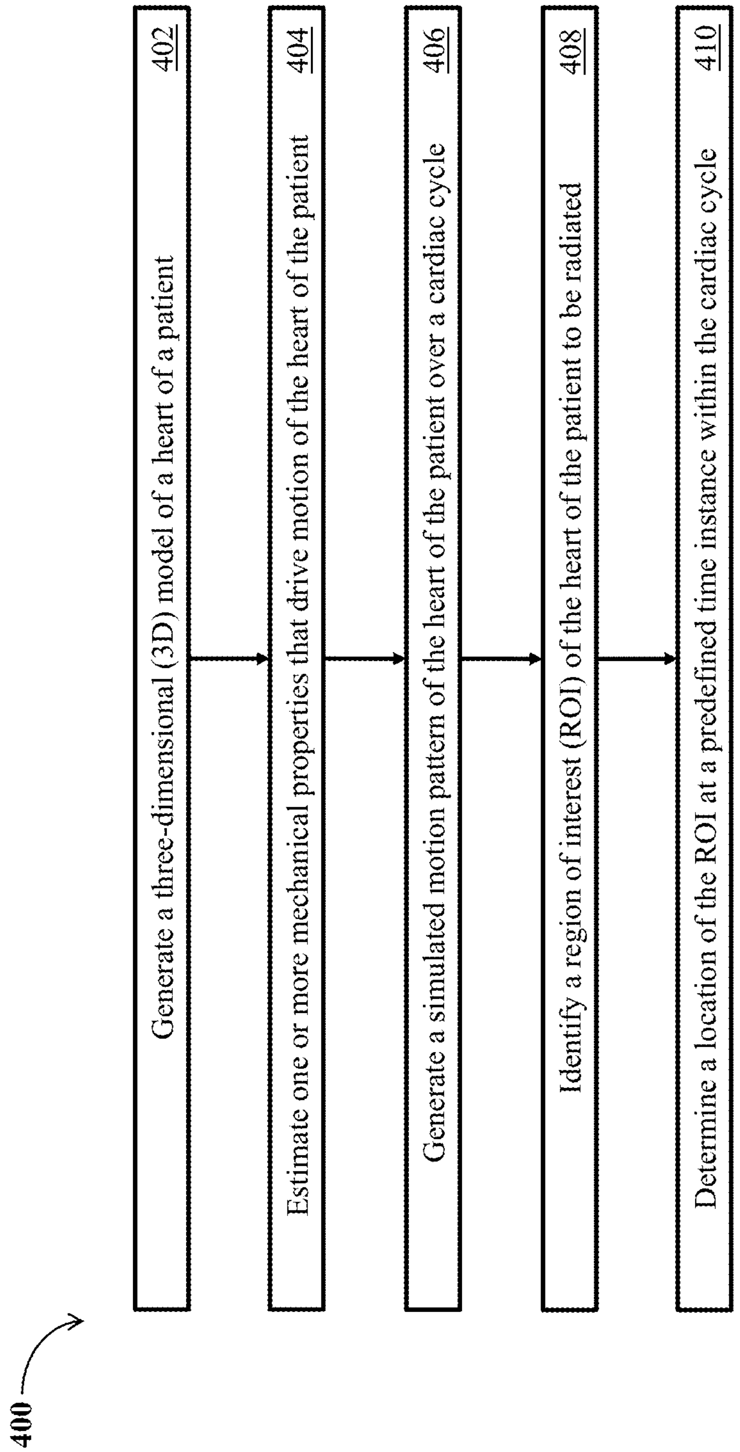
FIG. 4 is a flowchart illustrating a method of predicting locations of a target heart regions, according to an embodiment.

FIG. 4 shows a flowchart illustrating an embodiment of a method 400 of predicting a location of a target heart region for cardiac radiotherapy ablation, according to example embodiments. In brief overview, the method 400 can include generating a geometric model of a heart of a patient based on medical images of the patient (STEP 402), and estimating one or more mechanical properties of the heart of the patient (STEP 404). The method 400 can include generating a simulated motion pattern of the heart of the patient over at least part of a cardiac cycle (STEP 406), identifying a region of interest (ROI) of the heart of the patient to be radiated (STEP 408), and determining a location of the ROI at a predefined time instance within the cardiac cycle (STEP 410). The method 400 can be implemented by computing device(s) 116 or processor(s) thereof (e.g., processor 204).

Referring back to FIGS. 1-4, the method 400 can include the computing device(s) 116 or processor(s) 204 generating a geometric model of the heart of the patient based on medical images of the patient (STEP 402). Prior to the cardiac ablation procedure, the imaging device 110 can acquire image data 312 of the patient. The image data 312 can include cardiac gated CTA images, CT images, MR images, other types of medical images or a combination thereof. Also, the electrophysiology system 114 can record electrophysiological study data 314 of the patient depicting electrical activities of the patient's heart. The computing device 112 can store the image data 312 and the electrophysiology data 314 in database 106.

A doctor or other medical professional can mark or delineate the ROI on one or more of the acquired medical images of the patient, for example, based on the image data 312 and the electrophysiology data 314. For instance, the doctor can manually identify (e.g., over a display of computing device 112) or mark the boundary of the ROI to be radiated. On some implementations, the computing device 112 can process the marked image(s) to refine the boundary of the ROI, for example, using image segmentation algorithms, object identification algorithms, other image processing algorithms or a combination thereof. The computing device 112 may use the refined (or originally marked) ROI boundary to identify the ROI in other non-marked images of the patient. In some implementations, the doctor can mark the ROI on all acquired medical images.

In some implementations, the ROI can include or can be one or more segments of a standardized N-segment model where N is an integer. For instance, the standardized N-segment model can include the standardized AHA 17-segment heart model. The standardized N-segment model represents a standard geometrical description of the heart. The computing device 112 can identify the segments based on a parametric model of the heart chambers, for example, as described in "Four-Chamber Heart Modeling and Automatic Segmentation for 3-D Cardiac CT Volumes Using Marginal Space Learning and Steerable Features." IEEE Transactions on Medical Imaging 27, no. 11 (November 2008) 1668-81. In some implementations, other standardized geometrical models of the heart can be used. An operator of the computing device 112 can identify the ROI as one or more segments of the standardized N-segment model, e.g., via a user interface displayed by the computing device 112.

The medical images acquired by the imaging device 110 can be two-dimensional images. The processor 204 or the geometrical model generator 302 can generate a patient-specific geometrical model of the patient's heart using medical image data 312. The patient-specific geometrical model can include a three-dimension (3D) model depicting anatomical characteristics, e.g., shape, size and/or various anatomical regions, of the patient's heart. For instance, the processor 204 or the geometrical model generator 302 can generate a 3D mesh of the patient's heart using the medical images of the patient. The processor 204 or the geometrical model generator 302 can add one or more layers on top of the 3D mesh to reflect different regions or segments of the patient's heart.

In some implementations, the geometrical model generator 302 can be integrated within the cardiac therapy planning system 102. For instance, the imaging device 110 or the computing device 112 can generate the 3D model of the patient's heart and store the generated 3D model in the database 106. The processor 204 or the ROI positioning system 104 can obtain or access the generated 3D model from database 106. In some implementations, the processor 204 or the geometrical model generator 302 can register the electrophysiology data with the generated 3D model of the patient's heart. In some implementations, the processor 204 or the simulation model generator 302 can combine the electrophysiology data with the generated 3D model(s) of the patient's heart as described in U.S. Pat. No. 9,463,072, the content of which is incorporated herein by reference.

The processor 204 or the motion pattern estimator 304 can determine an estimated motion pattern of the heart of the patient over the cardiac cycle or a portion thereof, using the image data 312. For instance, the processor 204 or the geometrical model generator 302 can generate multiple 3D models depicting various deformation states of the patient's heart over the cardiac cycle or a portion thereof. Given a sequence of acquired medical images of the patient's heart, the processor 204 or the geometrical model generator 302 can generate, for each acquired medical image, a corresponding 3D model representing a deformation state of the heart (or simply a state of the heart) at the time instance (of the cardiac cycle) the medical image was acquired. The multiple 3D models of the heart corresponding to different time instances of the cardiac cycle can be viewed as a four-dimensional (4D) model of the patient's heart, with the fourth dimension representing time. The processor 204 or the motion pattern estimator 304 can track displacements of a discrete set of points of the heart over the sequence of generated 3D model (or the 4D model) of the patient's heart. The processor 204 or the motion pattern estimator 304 can select the set of points in one of the generated 3D models of the patient's heart, and employ motion tracking techniques to track the selected set of points over the sequence of 3D models. The processor 204 or the motion pattern estimator 304 can use mesh segmentation to select the set of points. The processor 204 or the motion pattern estimator 304 can select a set of points representing landmarks of the heart for motion tracking. In some implementations, the processor 204 or the motion pattern estimator 304 can select the set of points in an acquired image (or image frame), and track the selected points over the sequence of acquired image frames (e.g., two-dimensional (2D) images). The processor 204 or the motion pattern estimator 304 can map the set of points to a corresponding set of points in the sequences of 3D models of the patient's heart.

In some implementations, the processor 204 or the motion pattern estimator 304 can estimate the motion pattern of the patient's heart by estimating a displacement field based on image voxel values of the sequence of 3D models or the sequence of acquired image frames. The processor 204 or the motion pattern estimator 304 can employ deep learning techniques to estimate the displacement field, for example, as described in "Learning a Probabilistic Model for Diffeomorphic Registration." IEEE Transactions on Medical Imaging 38, no. 9 (September 2019): 2165-76. The estimated motion pattern depicts the motion of the patient's heart over the cardiac cycle or a portion thereof based on the acquired medical images of the patient.

The method 400 can include estimating one or more mechanical properties of the heart of the patient (STEP 404), and generating a simulated motion pattern of the heart of the patient over at least part of the cardiac cycle (STEP 406). The processor 204 or the mechanical properties estimator 306 can estimate mechanical properties of the patient's heart at various time instants of the cardiac cycle (or of a portion of the cardiac cycle) using electrophysiology data 314 and the generated geometrical (or 3D) model of the patient's heart. The processor 204 or the mechanical properties estimator 306 may further use other patient data 316 to estimate mechanical properties of the patient's heart. The processor 204 or the mechanical properties estimator 306 can analyze electrophysiology data 314 (and possibly other patient data 316) to extract measurements of electrical and mechanical activity in the patient's heart. Measurements of electrical activity can include total activation time of the left or right ventricle, measurements extracted from ECG data such as QRS duration, electrical axis, QT interval duration, point-wise activation times or electrical voltage values as measured by catheter devices as part of electro anatomical mapping. Measurements of mechanical activity can include blood pressure acquired invasively or non-invasively (e.g. via arm cuff), mechanical strain derived from strain imaging, displacement values derived from imaging. The processor 204 or the mechanical properties estimator 306 can simulate the corresponding measurements of electrical and mechanical activity and compare them with the measurements extracted from the data. The processor 204 or the mechanical properties estimator 306 can modify the electrical and mechanical properties of the heart of the patient as to minimize the difference between the simulated and data-based measurements of electrical and mechanical activity.

In a second step, the processor 204 or the mechanical properties estimator 306 modifies the mechanical properties of the heart of the patient as to minimize the difference between the simulated and data-based measurements of mechanical activity, using the electrical properties modified in the first step. Additional methods to modify the electrical and mechanical properties of the patient's heart as to minimize the difference between simulated and data-based measurements of electrical and mechanical activity are disclosed in U.S. Pat. Nos. 9,129,053, 9,245,091, 10,733,910. The mechanical properties can include contraction forces or pressures that drive the motion of the patient's heart during the contraction phase and relaxation (or elasticity) forces or pressures that drive the motion of the patient's heart during the relaxation phase. The contraction forces/pressures or the relaxation forces/pressures at a given time instance within the cardiac cycle are correlated with or dependent on the electrical activity of the heart at the same time instance. In particular, the electrical activity of the heart triggers or produces the contraction forces/pressures or the relaxation forces/pressures, which in turn drive the motion of the heart. As the electrical activity of the heart changes over time so do the forces/pressures driving the motion of the heart.

Given the estimated forces/pressures at a given time instance, the processor 204 or the motion pattern simulator 308 can be configured to determine the motion produced by the estimated forces/pressures at different points or regions of the heart. In particular, given a distribution of the forces/pressures over the patient's heart at the time instance, the processor 204 or the motion pattern simulator 308 can compute displacements of various regions or fragments of the 3D model of patient's heart (e.g., the 3D model corresponding to the time instance) according to the local forces or pressures. The computed displacements can represent movements of the various regions or fragments of the 3D model over a time interval, such as the time interval between two consecutive 3D models or between two consecutive image frames.

In general, given a generated 3D model of the patient's heart at time instance $t_0$, the processor 204 or the motion pattern simulator 308 can compute the displacements of various regions or fragments of the 3D model between time instance $t_0$ and time instance $t_1$ ($t_1 > t_0$) based on estimated mechanical properties of the patient's heart at time instance $t_0$ or within the time interval [$t_0$ to $t_1$]. In some implementations, the processor 204 or the mechanical properties estimator 306 can estimate the mechanical properties at discrete time points, and assume that the mechanical properties are constant within intervals between consecutive time points. The processor 204 or the motion pattern simulator 308 can deform the 3D model corresponding to time instance $t_0$ according to the computed displacements to determine a simulated state (or simulated deformation state) of the patient's heart at time instance $t_1$.

In some implementations, the mechanical properties estimator 306 and the motion pattern simulator 308 can operate together in an iterative manner to estimate the mechanical properties and the simulated motion pattern of the heart. For instance, the processor 204 or the mechanical properties estimator 306 can estimate the mechanical properties of the patient's heart using the generated 3D model and the electrophysiology data 314, and the processor 204 or the motion pattern simulator 308 can generate a motion pattern of the patient's heart using the 3D model and the electrophysiology data 314. The processor 204 may further use the other patient data 316 in estimating the mechanical properties of the patient's heart and/or generating the motion pattern of the patient's heart. The processor 204 or the motion pattern comparator 310 can compare the estimated motion pattern generated by the motion pattern estimator 304 and the simulated motion pattern generated by the motion pattern simulator 308. If the estimated motion pattern and the simulated motion pattern are not sufficiently similar (e.g., based on one or more thresholds), the processor 204 or the mechanical properties estimator 306 can adjust the estimated mechanical properties and a new simulated motion pattern is determined by the processor 204 or the motion pattern simulator 308 based on the adjusted mechanical properties. The motion pattern comparator 310 can compare the estimated motion pattern and the new simulated motion pattern. The processor 204 can repeat these steps (e.g., adjusting the mechanical properties, updating the simulated motion pattern and comparing the estimated and simulated motion patterns) until both motion patterns are close enough.

In comparing the estimated and simulated motion patterns, the processor 204 or the comparator 310 can select or identify one or more estimated states (also referred to herein as ground truth positions or ground truth states) of the patient's heart based on the generated 3D model and the estimated motion pattern. Each estimated state represents a deformation and/or position state of the patient's heart determined by applying the estimated motion pattern to the generated 3D model of the patient's heart. For instance, estimated state $S_{i,e}$ can represent a deformation and/or position state of the patient's heart determined by applying the estimated motion pattern to the generated 3D model of the patient's heart up to time instance $t_i$ of the cardiac cycle, where i is an integer. The processor 204 or the comparator 310 can select or identify one or more simulated states by applying the simulated motion pattern to the generated 3D model of the patient's heart. Each simulated state corresponds to one of the estimated states. For example, simulated state $S_{i,s}$ and estimated state $S_{i,e}$ represent states of the patient's heart at time instance $t_i$. Each of the estimated and simulated states represents a deformation of the generated 3D model. The processor 204 or the motion pattern comparator 310 can compare one or more distances between the simulated state $S_{i,s}$ and the estimated state $S_{i,e}$. The processor 204 or the motion pattern comparator 310 can compare point-wise distances, point-to-curve (also referred to as point-to-surface) distances or curve-to-curve (also referred to as surface-to-surface) between the simulated state $S_{i,s}$ and the estimated state $S_{i,e}$ to a threshold. If the distance(s) is less than the threshold, the simulated state $S_{i,s}$ and the estimated state $S_{i,e}$ are determined to be sufficiently similar, otherwise the steps of adjusting the mechanical properties, updating the simulated motion pattern and comparing the estimated and simulated motion patterns are repeated in another iteration. In the iterative approach, the processor 204 can set initial estimates of the mechanical properties based on a random guess, literature data and/or patient information (e.g., demographic and/or medical information).

Figure 5:
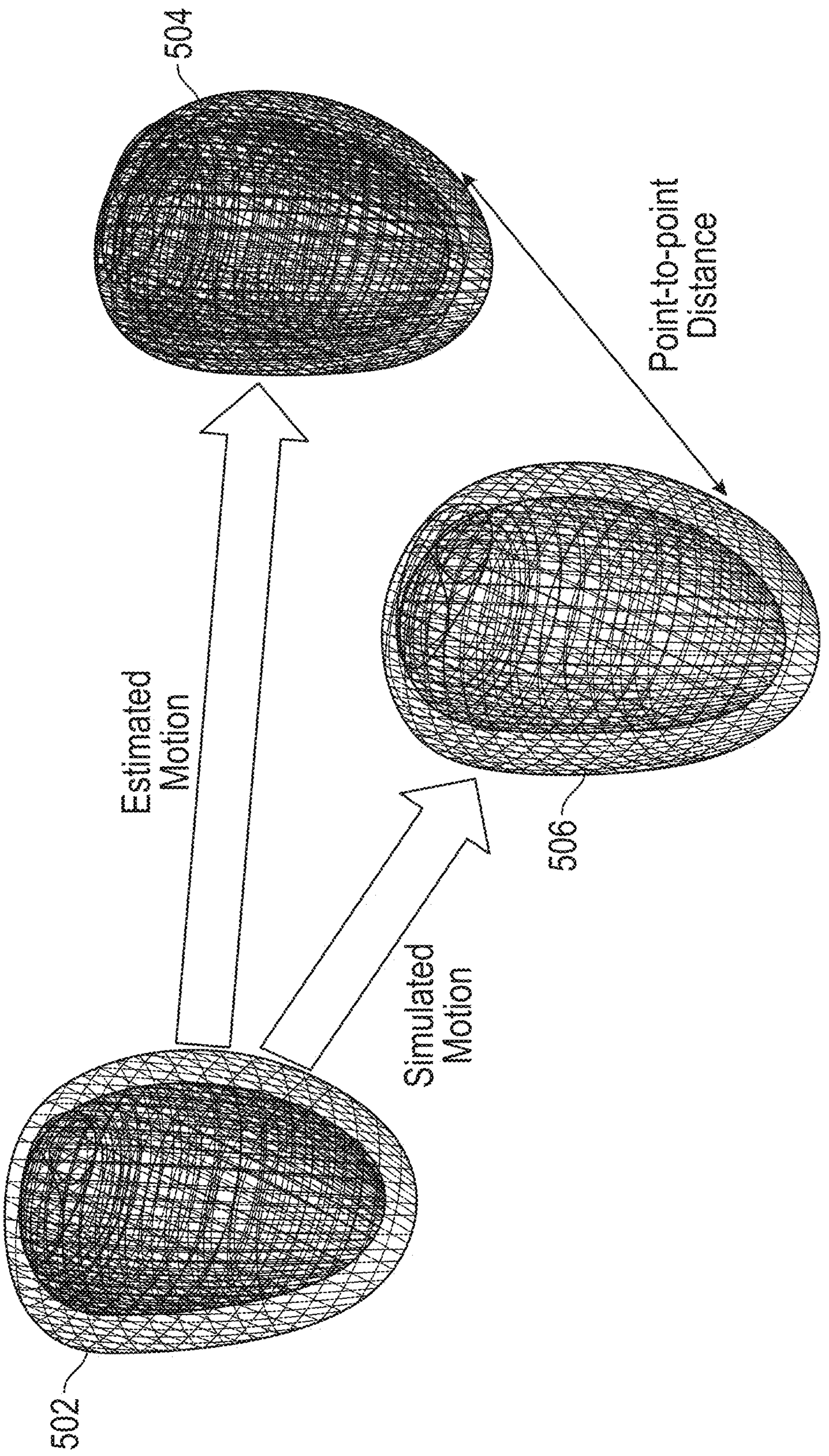
FIG. 5 shows a diagram illustrating estimated and simulated states of a heart, according to an embodiment.

Referring now to FIG. 5, a diagram illustrating estimated and simulated states of the patient's heart are shown, according to example embodiments. The 3D shape 502 represents an example of the 3D model (or geometrical model) of the patient's heart generated at step 402. The 3D shape 504 represents an example of an estimated state of the patient's heart that is generated by applying the estimated motion pattern (e.g., up to a time instance $t_i$ of the cardiac cycle) to the 3D model 502. The 3D shape 506 represents an example of simulated state of the patient's heart that is generated by applying the simulated motion pattern (e.g., up to a time instance $t_i$ of the cardiac cycle) to the 3D model 502. The simulated state 506 is expected to converge toward the estimated state 504 after a number of iterations of adjusting the mechanical properties and updating the simulated state.

Figure 6B:
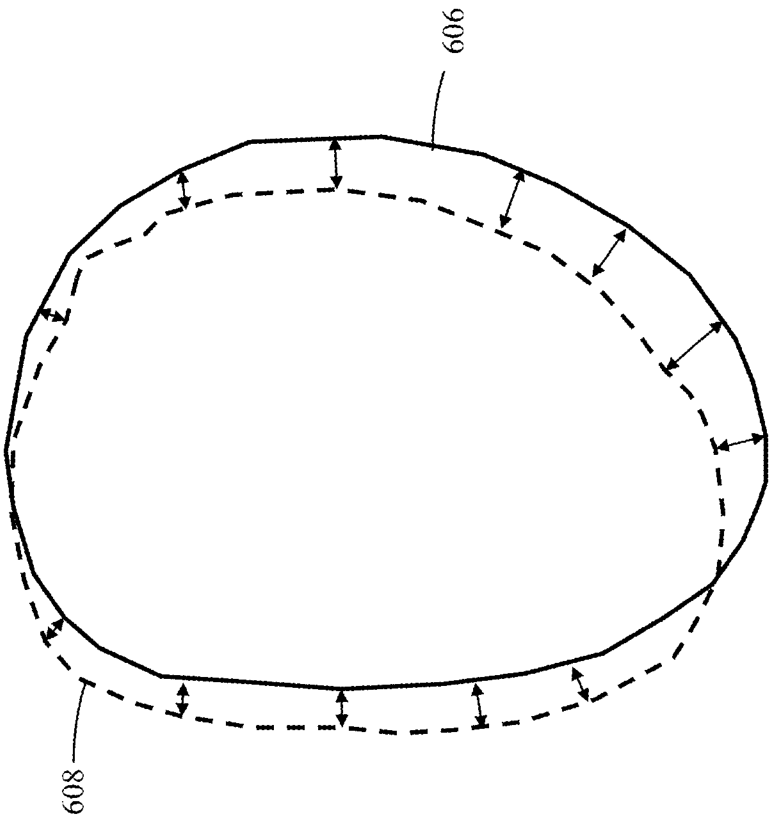
FIGS. 6A and 6B show diagrams illustrating distances between estimated and simulated states of the heart, according to an embodiment.
Figure 6A:
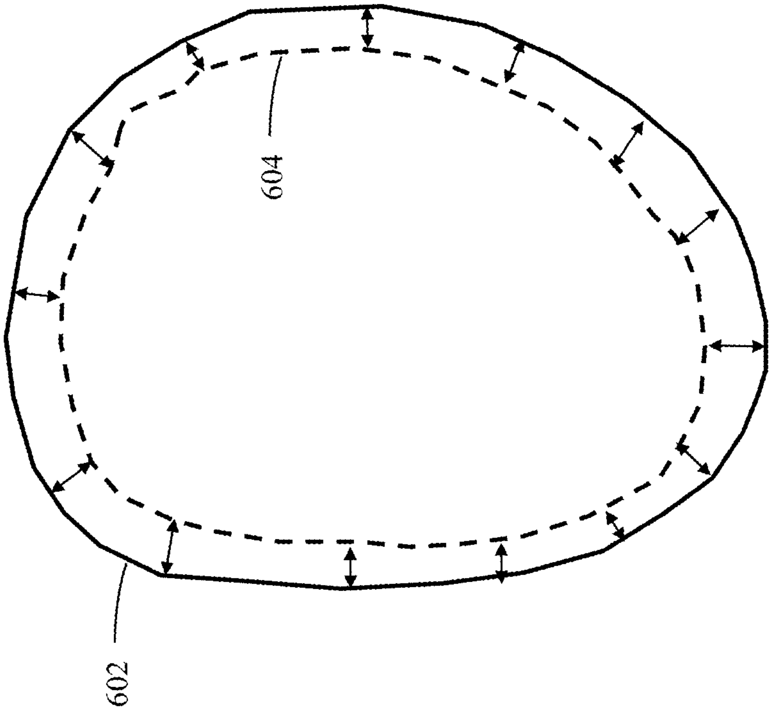

Referring now to FIGS. 6A and 6B, diagrams illustrating distances between example estimated and simulated states of the heart are shown, according to an embodiment. With regard to FIG. 6A, the curve 602 is a 2D representation of the estimated state of the heart while the curve 604 is a 2D representation of the simulated state of the heart. The arrows between the two curves 602 and 604 represent distances between the two curves. These distances can be point-wise distances (e.g., distances between pairs of points with each pair including a point of the simulated state 604 and point of the estimated state 602), point-to-surface distances or surface-to-surface distances. The motion pattern comparator 310 can compare the distances between the estimated and simulated states 602 and 604 to a threshold, and determine the two states to be similar if the distances (or a maximum thereof) is below the threshold, otherwise continue adjusting the estimated mechanical properties and updating the simulated motion pattern until the two states are sufficiently similar. FIG. 6B illustrates another example of 2D representations of an estimated state 606 and a simulated state 608. The arrows between the curves 606 and 608 represent distances between both states of the patient's heart.

In comparing the distances between estimated states and simulated states, the processor 204 or the motion pattern comparator 310 can evaluate the distances between estimated states and corresponding simulated states at any given time over the cardiac cycle, and compare each of the evaluated distances to the threshold. In some implementations, the processor 204 or the motion pattern comparator 310 can average distances over multiple time points of the cardiac cycle and compare the average distances to the threshold.

In some implementations, the processor 204 can perform the comparison of the estimated and simulated heart states over separate time intervals corresponding to the time ranges between consecutive image frames. For two time instances $t_1$ and $t_2$ corresponding to two consecutive image frames $F_1$ and $F_2$, the processor 204 or the motion pattern estimator 304 can deform a 3D model of the patient's heart corresponding to time instance $t_1$ according to the estimated motion pattern to determine the estimated state of the heart at time instance $t_2$. The processor 204 can then deform the 3D model of the patient's heart corresponding to time instance $t_1$ according to the simulated motion pattern to determine the simulated state of the heart at time instance $t_2$. The processor 204 can iteratively adjust the mechanical properties of the heart and update the simulated motion pattern until the estimated and simulated states at time instance $t_2$ are sufficiently similar (e.g., distances are below the threshold). In other words, the mechanical properties of the cardiac tissue are adjusted to minimize the distances between the estimated and simulated states at the time instance $t_2$. The processor 204 can repeat this process for various time instance pairs $(t_i, t_{i+1})$ corresponding to pairs of consecutive image frames $(F_i, F_{i+1})$. This approach leads to multiple estimated values of the mechanical properties of the cardiac tissue over the cardiac cycle (e.g., a set of estimated mechanical properties for each time instance pairs $(t_i, t_{i+1})$). The processor 204 can define the global optimal values as the mean or median values.

In some implementations, the processor 204 can employ a plurality of stochastic variations of the mechanical and electrical properties of the cardiac tissues originally estimated from available measurements. The processor 204 can generate a plurality of simulated motion patterns based on the plurality of stochastic variations of the mechanical and electrical properties of the cardiac tissues. The processor 204 can compare each of the plurality of simulated motion patterns to the estimated motion patterns based on distances between simulated states associated with different simulated motion patterns and an estimated state. The processor 204 can select the simulated motion pattern that minimizes the distances between the corresponding simulated state and the estimated state.

In some implementations, the processor 204 or the motion pattern simulator 308 can employ a machine learned model. The machine learned model can use a synthetically generated database of cardiac motions produced using the 3D model of the heart, electrophysiology data 314 and other data 316 of the patient. The synthetically generated database of cardiac motions can be produced using patient-specific data (e.g., image data 312 and physiological data 314 of the patient) or using data from a plurality of patients. For instance, the synthetically generated database of cardiac motions can be produced using one 3D model of the heart or a combination of multiple models from the plurality of patients and a set of values representing physical (e.g., electrical and mechanical) properties of the cardiac tissue randomly sampled from the data of the plurality of patients. The machine learned model or the data-driven motion model can be configured to express the position of each point of the heart at a given time $t_{i+1}$ as a function of the position of the same point at the previous time instance $t_i$, the physical properties of the cardiac tissue associated with the point as well as the estimated or measured location of the same point at time $t_{i+1}$. In the synthetically generated database of cardiac motions, multiple examples of cardiac motions can be produced based on simulated states of the heart with the addition of random perturbation simulating the effect of noise. The machine learned model is configured to minimize distances between states of the heart generated by the machine learned model and corresponding simulated states over a multitude of time instances. Referring back to FIG. 3, once trained the machine learned model can be used by the motion pattern simulator 308 in place of simulation.

Referring back to FIG. 4, the method 400 can include identifying the region of interest (ROI) of the heart of the patient to be radiated (STEP 408), and determining a location of the ROI at a predefined time instance within the cardiac cycle (STEP 410). The processor 204 can identify the ROI in a plurality of simulated states that are determined by applying the final simulated motion pattern to the 3D model generated at step 402. The processor 204 can map the ROI identified or marked in the acquired images or image frames into the simulated states. The processor 204 can use an image mask to indicate the location of the ROI in each of the simulated states.

The processor 204 can provide the simulated motion pattern and/or the plurality of simulated states to the cardiac radiotherapy planning system 102 or the respective computing device 112. In some implementations, the identification of the ROI within simulated states can be performed by the computing device 112. The computing device 112 can use the simulated motion pattern or the corresponding simulated states to determine a location of the ROI at one or more time instances of the cardiac cycle. The one or more time instances of the cardiac cycle can represent time instances during which a radiation beam will be applied to the ROI. Given the locations of the ROI, the cardiac radiotherapy planning system 102 or the computing device 112 can accurately target or radiate the ROI while sparing surrounding or intervening tissue as much as possible.

The final simulated motion pattern (output by the ROI positioning system 104) is optimized to mimic or reproduce the real or actual motion of the patient's heart. The final simulated motion pattern is used by the cardiac radiotherapy planning system 102 or the computing device 112 to estimate the position of the ROI for radiation therapy, under conditions encountered during radiation therapy treatment. In most clinical workflows, the patient is immobilized during radiation therapy delivery by applying rigid or vacuum-based immobilization, abdominal compression and/or shoulder mask, with or without anesthesia. In some implementations, the computing device(s) 116 or the computing device 112 can model the immobilization conditions as boundary conditions incorporated in the simulated motion pattern. The boundary conditions can act as constraints to the heart displacement inside the torso. Boundary conditions can be expressed for instance as prescribed pressure on the epicardial surface or as opposing displacement along predefined directions.

One should note that the examples discussed in this specification are provided for illustrative purposes and are not to be interpreted as limiting. For example, other techniques can be used to estimate or adjust the mechanical properties of the heart. Also, other types of distances can be used to compare simulated states and corresponding estimated states.

Each method described in this disclosure, such as method 400 of FIG. 4, can be carried out by computer code instructions stored on computer-readable medium. The computer code instructions, when executed by one or more processors of a computing device, can cause the computing device to perform that method.

While the disclosure has been particularly shown and described with reference to specific embodiments, it should be understood by those skilled in the art that various changes in form and detail may be made therein without departing from the spirit and scope of the invention described in this disclosure.

While this disclosure contains many specific embodiment details, these should not be construed as limitations on the scope of any inventions or of what may be claimed, but rather as descriptions of features specific to particular embodiments of particular inventions. Certain features described in this specification in the context of separate embodiments can also be implemented in combination in a single embodiment. Conversely, various features described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated in a single software product or packaged into multiple software products.

References to "or" may be construed as inclusive so that any terms described using "or" may indicate any of a single, more than one, and all of the described terms.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain embodiments, multitasking and parallel processing may be advantageous.

What is claimed is:

1. A method of predicting a location of target heart region for cardiac ablation, the method comprising:

generating, by one or more processors, a three-dimensional (3D) model of a heart of a patient based on medical images of the patient;

estimating, by the one or more processors using the 3D model of the heart and electrophysiology data of the patient, one or more mechanical properties that drive motion of the heart of the patient;

generating, by the one or more processors using the 3D model and the one or more mechanical properties, a simulated motion pattern of the heart of the patient over a cardiac cycle;

iteratively refining, by the one or more processors, the simulated motion pattern within the 3D model based at least in part on a comparison between the simulated motion pattern and an estimated motion pattern derived from the medical images;

identifying, by the one or more processors, a region of interest (ROI) of the heart of the patient to be radiated;

determining, by the one or more processors using the simulated motion pattern of the heart of the patient, a location of the ROI at a predefined time instance within the cardiac cycle; and outputting, by the one or more processors, a treatment planning parameter configured for use by a cardiac radiotherapy planning system, the treatment planning parameter specifying at least one of beam geometry, beam intensity, dose distribution, or timing of beam delivery relative to the cardiac cycle, thereby causing the cardiac radiotherapy planning system to conduct a cardiac ablation treatment that targets the ROI while reducing radiation exposure to surrounding or an intervening tissue.

2. The method of claim 1, wherein the one or more mechanical properties include contraction forces and relaxation forces of the heart of the patient.

3. The method of claim 1, wherein the medical images include a sequence of image frames acquired over a time interval, and the method further comprising:

determining, by the one or more processors using the sequence of image frames, an estimated motion pattern of the heart of the patient over the cardiac cycle.

4. The method of claim 3, wherein determining the estimated motion pattern includes:

tracking displacements of a discrete set of points of the heart over the sequence of image frames; or estimating, using a machine learning model, a displacement field using the sequence of image frames.

5. The method of claim 3, comprising:

determining, using the estimated motion pattern of the heart of the patient, one or more estimated positions of one or more points of the heart of the patient at a time point of the cardiac cycle;

determining, using the simulated motion pattern of the heart of the patient, one or more simulation positions of the one or more points of the heart of the patient at the time point of the cardiac cycle;

computing one or more point-wise distances between the one or more simulation positions and the one or more estimated positions;

updating the one or more mechanical properties of the heart of the patient, upon determining that the one or more point-wise distances exceed a threshold value; and updating the simulated motion pattern of the heart of the patient based on the updated one or more mechanical properties.

6. The method of claim 5 further comprising:

repeating the steps of determining the one or more simulation positions, computing the one or more point-wise distances, updating the one or more mechanical properties and updating the simulated motion pattern of the heart of the patient until the one or more point-wise distances are below the threshold value.

7. The method of claim 5, wherein determining the one or more estimated positions includes:

deforming, according to the estimated motion pattern of the heart of the patient, a 3D model of the heart corresponding to a time instance to $t_0$ determine an estimated 3D model of the heart corresponding to a time instance $t_1$, the estimated 3D model indicative of an estimated state of the heart at the time instance $t_1$; and identifying the one or more estimated positions on the estimated 3D model of the heart corresponding to the time instance $t_1$, and wherein determining the one or more simulation positions includes:

deforming, according to the simulated motion pattern of the heart of the patient, the 3D model of the heart corresponding to the time instance to $t_0$ determine a simulated 3D model of the heart corresponding to the time instance $t_1$, the simulated 3D model indicative of a simulated state of the heart at the time instance $t_1$; and identifying the one or more simulation positions on the simulated 3D model of the heart corresponding to the time instance $t_1$.

8. The method of claim 7, comprising:

repeating the steps of determining the one or more estimated positions and determining the one or more simulation positions for a plurality of time instance pairs $(t_0, t_1)$ corresponding to pairs of consecutive image frames in the sequence of image frames;

computing a plurality of point-wise distances between the one or more simulation positions and corresponding estimated positions across the plurality of time instance pairs $(t_0, t_1)$; and updating the one or more mechanical properties of the heart of the patient, upon determining that the plurality of point-wise distances exceed the threshold value.

9. The method of claim 5, wherein updating the one or more mechanical properties of the heart of the patient includes:

generating a plurality of second simulated motion patterns of the heart corresponding to various variations of the one or more mechanical properties and various variations of electrical properties of the heart;

determining, for each second simulated motion pattern, one or more corresponding simulation positions of the one or more points of the heart of the patient at the time point of the cardiac cycle;

computing, for each second simulated motion pattern, one or more corresponding point-wise distances between the one or more corresponding simulation positions and the one or more estimated positions;

selecting a second simulated motion pattern of the plurality of second simulated motion patterns based on the one or more corresponding point-wise distances; and updating the one or more mechanical properties according to variations of the one or more mechanical properties corresponding to the selected second simulated motion pattern.

10. The method of claim 1, wherein the ROI includes one or more segments of a standardized N-segment model where N is an integer.

11. The method of claim 1, further comprising modeling immobilization conditions to be applied to the patient during a cardiac ablation procedure as boundary conditions incorporated in the simulated motion pattern of the heart of the patient.

12. The system of claim 11, wherein the ROI includes one or more segments of a standardized N-segment model where N is an integer.

13. A system for predicting a location of target heart region for cardiac ablation, the system comprising:

one or more processors; and a memory to store computer code instructions, the computer code instructions when executed cause the one or more processors to:

generate a three-dimensional (3D) model of a heart of a patient based on medical images of the patient;

estimate, using the 3D model of the heart and electrophysiology data of the patient, one or more mechanical properties that drive motion of the heart of the patient;

generate, using the 3D model and the one or more mechanical properties, a simulated motion pattern of the heart of the patient over a cardiac cycle;

iteratively refine the simulated motion pattern within the 3D model based at least in part on a comparison between the simulated motion pattern and an estimated motion pattern derived from the medical images;

identify a region of interest (ROI) of the heart of the patient to be radiated;

determine, using the simulated motion pattern of the heart of the patient, a location of the ROI at a predefined time instance within the cardiac cycle; and output a treatment planning parameter configured for use by a cardiac radiotherapy planning system, the treatment planning parameter specifying at least one of beam geometry, beam intensity, dose distribution, or timing of beam delivery relative to the cardiac cycle, thereby causing the cardiac radiotherapy planning system to conduct a cardiac ablation treatment that targets the ROI while reducing radiation exposure to surrounding or an intervening tissue.

14. The system of claim 13, wherein the one or more mechanical properties include contraction forces and relaxation forces of the heart of the patient.

15. The system of claim 13, wherein the medical images include a sequence of image frames acquired over a time interval, and the one or more processors are further configured to:

determine, using the sequence of image frames, an estimated motion pattern of the heart of the patient over the cardiac cycle.

16. The system of claim 15, wherein when determining the estimated motion pattern the one or processors are configured to:

track displacements of a discrete set of points of the heart over the sequence of image frames; or estimate, using a machine learning model, a displacement field using the sequence of image frames.

17. The system of claim 15, wherein the one or more processors are configured to:

determine, using the estimated motion pattern of the heart of the patient, one or more estimated positions of one or more points of the heart of the patient at a time point of the cardiac cycle;

determine, using the simulated motion pattern of the heart of the patient, one or more simulation positions of the one or more points of the heart of the patient at the time point of the cardiac cycle;

compute one or more point-wise distances between the one or more simulation positions and the one or more estimated positions;

update the one or more mechanical properties of the heart of the patient, upon determining that the one or more point-wise distances exceed a threshold value; and update the simulated motion pattern of the heart of the patient based on the updated one or more mechanical properties.

18. The system of claim 17, wherein the one or more processors are configured to:

repeat the steps of determining the one or more simulation positions, computing the one or more point-wise distances, updating the one or more mechanical properties and updating the simulated motion pattern of the heart of the patient until the one or more point-wise distances are below the threshold value.

19. The system of claim 18, wherein when determining the one or more estimated positions, the one or more processors are configured to:

deform, according to the estimated motion pattern of the heart of the patient, a 3D model of the heart corresponding to a time instance to $t_0$ determine an estimated 3D model of the heart corresponding to a time instance $t_1$, the estimated 3D model indicative of an estimated state of the heart at the time instance $t_1$; and identify the one or more estimated positions on the estimated 3D model of the heart corresponding to the time instance $t_1$, and wherein determining the one or more simulation positions includes:

deform, according to the simulated motion pattern of the heart of the patient, the 3D model of the heart corresponding to the time instance to $t_0$ determine a simulated 3D model of the heart corresponding to the time instance $t_1$, the simulated 3D model indicative of a simulated state of the heart at the time instance $t_1$; and identify the one or more simulation positions on the simulated 3D model of the heart corresponding to the time instance $t_1$.

20. The system of claim 19, wherein the one or more processors are further configured to:

repeat the steps of determining the one or more estimated positions and determining the one or more simulation positions for a plurality of time instance pairs ($t_0$, $t_1$) corresponding to pairs of consecutive image frames in the sequence of image frames;

compute a plurality of point-wise distances between the one or more simulation positions and corresponding estimated positions across the plurality of time instance pairs ($t_0$, $t_1$); and update the one or more mechanical properties of the heart of the patient, upon determining that the plurality of point-wise distances exceed the threshold value.

21. The system of claim 18, wherein when updating the one or more mechanical properties of the heart of the patient, the one or more processors are configured to:

generate a plurality of second simulated motion patterns of the heart corresponding to various variations of the one or more mechanical properties and various variations of electrical properties of the heart;

determine, for each second simulated motion pattern, one or more corresponding simulation positions of the one or more points of the heart of the patient at the time point of the cardiac cycle;

compute, for each second simulated motion pattern, one or more corresponding point-wise distances between the one or more corresponding simulation positions and the one or more estimated positions;

select a second simulated motion pattern of the plurality of second simulated motion patterns based on the one or more corresponding point-wise distances; and update the one or more mechanical properties according to variations of the one or more mechanical properties corresponding to the selected second simulated motion pattern.

22. The system of claim 13, wherein the one or more processors are further configured to model immobilization conditions to be applied to the patient during a cardiac ablation procedure as boundary conditions incorporated in the simulated motion pattern of the heart of the patient.

23. A non-transitory computer-readable medium including computer code instructions stored thereon, the computer code instructions when executed cause one or more processors to:

generate a three-dimensional (3D) model of a heart of a patient based on medical images of the patient;

estimate, using the 3D model of the heart and electrophysiology data of the patient, one or more mechanical properties that drive motion of the heart of the patient;

generate, using the 3D model and the one or more mechanical properties, a simulated motion pattern of the heart of the patient over a cardiac cycle;

iteratively refine the simulated motion pattern within the 3D model based at least in part on a comparison between the simulated motion pattern and an estimated motion pattern derived from the medical images;

identify a region of interest (ROI) of the heart of the patient to be radiated;

determine, using the simulated motion pattern of the heart of the patient, a location of the ROI at a predefined time instance within the cardiac cycle; and output a treatment planning parameter configured for use by a cardiac radiotherapy planning system, the treatment planning parameter specifying at least one of beam geometry, beam intensity, dose distribution, or timing of beam delivery relative to the cardiac cycle, thereby causing the cardiac radiotherapy planning system to conduct a cardiac ablation treatment that targets the ROI while reducing radiation exposure to surrounding or an intervening tissue.

* * * * *